United States Patent [19]
Charlton et al.

[11] Patent Number: 5,798,031
[45] Date of Patent: Aug. 25, 1998

[54] ELECTROCHEMICAL BIOSENSOR

[75] Inventors: Steven C. Charlton, Osceola; Larry D. Johnson, Elkhart; Matthew K. Musho, Granger; Dennis Slomski, South Bend, all of Ind.

[73] Assignee: Bayer Corporation, Elkhart, Ind.

[21] Appl. No.: 854,439

[22] Filed: May 12, 1997

[51] Int. Cl.$^6$ .................................................. G01N 27/26
[52] U.S. Cl. .................. 204/403; 435/187.1; 435/189.1;
    435/817; 156/73.1; 156/73.5; 156/102;
    156/106; 156/107; 156/196; 156/217; 156/219;
    156/220
[58] Field of Search .................. 204/403; 435/817,
    435/187.1, 189.1; 156/73.1, 73.5, 102,
    106, 107, 196, 217, 219, 220

[56] References Cited

U.S. PATENT DOCUMENTS 5,120,420  6/1992  Nankai et al. .......................... 204/403
5,141,868  8/1992  Shanks et al. .......................... 435/288
5,264,103  11/1993 Yoshioka et al. ....................... 204/403
5,628,890  5/1997  Carter et al. .......................... 204/403

*Primary Examiner*—Bruce F. Bell
*Attorney, Agent, or Firm*—Jerome L. Jeffers

[57] ABSTRACT

The present invention concerns an electrochemical sensor made up of an insulating base having an electrode layer on its surface and a lid of deformable material which comprises a concave area in the central portion thereof, so that when it is mated with the base, the lid and base form a capillary space containing the electrode layer. When the electrode layer is in operative contact with a reaction layer comprising an enzyme which will cause the production of mobile electrons when contacted with a suitable analyte, the concentration of analyte, e.g. glucose in blood, can be measured by measuring the current created by the flow of mobile electrons when contacted with a suitable analyte, the concentration of analyte, e.g. glucose in blood, can be measured by measuring the current created by the flow of mobile electrons.

25 Claims, 1 Drawing Sheet

ELECTROCHEMICAL BIOSENSOR

BACKGROUND OF THE INVENTION

The present invention relates to an electrochemical biosensor that can be used for the quantitation of a specific component (analyte) in a liquid sample and to a method of manufacturing such a biosensor. Electrochemical biosensors of the type under consideration are disclosed in U.S. Pat. Nos. 5,120,420 and 5,264,103. The devices disclosed in these patents have an insulating base upon which carbon electrodes are printed which electrodes are covered with a reagent layer which comprises a hydrophilic polymer in combination with an oxidoreductase specific for the analyte. There is typically a spacer element placed on the base, which element is cut out to provide a generally U shaped piece and a cover piece, so that when the base, spacer element and cover piece are laminated together, there is created a capillary space containing the electrodes and the reagent layer. In addition to the oxidoreductase, there is included an electron acceptor on the reagent layer or in another layer within the capillary space. A hydrophilic polymer, e.g. carboxymethyl cellulose, is used to facilitate the drawing of the aqueous test fluid into the capillary space.

In U.S. Pat. No. 5,141,868 there is disclosed another sensor in which the electrodes are contained within a capillary gap. This reference describes the preferred method of preparing the sensor as mating the base and cover plates using a resin comprising solid particles, such as fine glass particles, to ensure the desired spacing between them to thereby form the gap. There is also described forming the sensors from glass or plastic sheeting and it is stated that "where plastic sheeting is used, it can be in the form of precision mouldings, e.g. provided with spacers such as ridges to achieve controlled spacing of the component walls of the capillary cavities."

The present invention is concerned with an electrochemical sensor which is comprised of two parts; a lower part (base) which carries the electrode structure and reactants which are deposited as necessary and an upper part (lid) which is embossed to form three sides of a capillary space with the base forming the fourth side upon mating of the lid and base. The base and lid are laminated together, such as, by means of a heat activated adhesive coating on the lid or sonic welding. The sensor is used by dipping the open end of the capillary into a small drop of test fluid, such as blood, which is drawn into the capillary tube so that it covers the enzyme and electron acceptor on the electrode's surface. In a preferred embodiment, the electrode carries an oxidoreductase and an electron acceptor distributed in a hydratable polymeric matrix on its surface. Due to the hydratable nature of the polymer matrix, it disperses in the aqueous test fluid thereby allowing the oxidoreductase, which is glucose oxidase when the sensor is designed to determine the concentration of glucose in blood, to oxidize the analyte and the electron acceptor to shuttle the excess electrons to the working electrode thereby creating a measurable current which is proportionate to the concentration of analyte in the test fluid.

The two piece sensor construction of the present invention does not require an enzymatic layer. For example, there is a general category of sensors that detect directly at the electrode surface. Examples of such sensors would be those for detecting hematocrit or a sensor for detecting lead in blood. Another class of sensors is those which have a binding or coupling agent over or on the electrode surface which initiates a chemical reaction. Thus, a sensor with a binding agent capable of releasing a detectable moiety such as protons when the analyte attaches itself to the agent and measuring the pH change can be prepared according to the present invention. Alternatively, the binding system can be an antigen-antibody pair wherein the antibody could prevent or enhance a reaction at the electrode surface.

The manufacture of the prior art sensors as described above involves the use of an extra part, the spacer layer, and a number of processing steps which are not required with the two part sensor (base and lid) with which the present invention is involved. The present sensor is prepared by a straight forward procedure which involves the steps of:

a) printing the electrodes onto the base material.

b) coating the electrodes with the polymeric matrix containing the oxidoreductase and the electron acceptor.

c) coating an adhesive layer onto the lid.

d) embossing the lid, to create a concave area therein with flat surfaces surrounding it.

e) heat sealing the lid onto the base.

SUMMARY OF THE INVENTION

The present invention is an electrochemical sensor for the detection of an analyte in a fluid test sample which comprises:

a) an insulating base plate;

b) an electrode layer on the base plate; and c) a lid of deformable material which provides a concave area in a portion thereof while leaving a flat surface surrounding the concave portion in such a manner that, when mated with the base, the lid and base form a capillary space in which the enzyme is available for direct contact with the fluid test sample which is drawn into the capillary space by capillary action.

Typically, the electrode is in operative connection with an enzyme which reacts with the analyte to produce mobile electrons.

DESCRIPTION OF THE INVENTION

Figure 1:
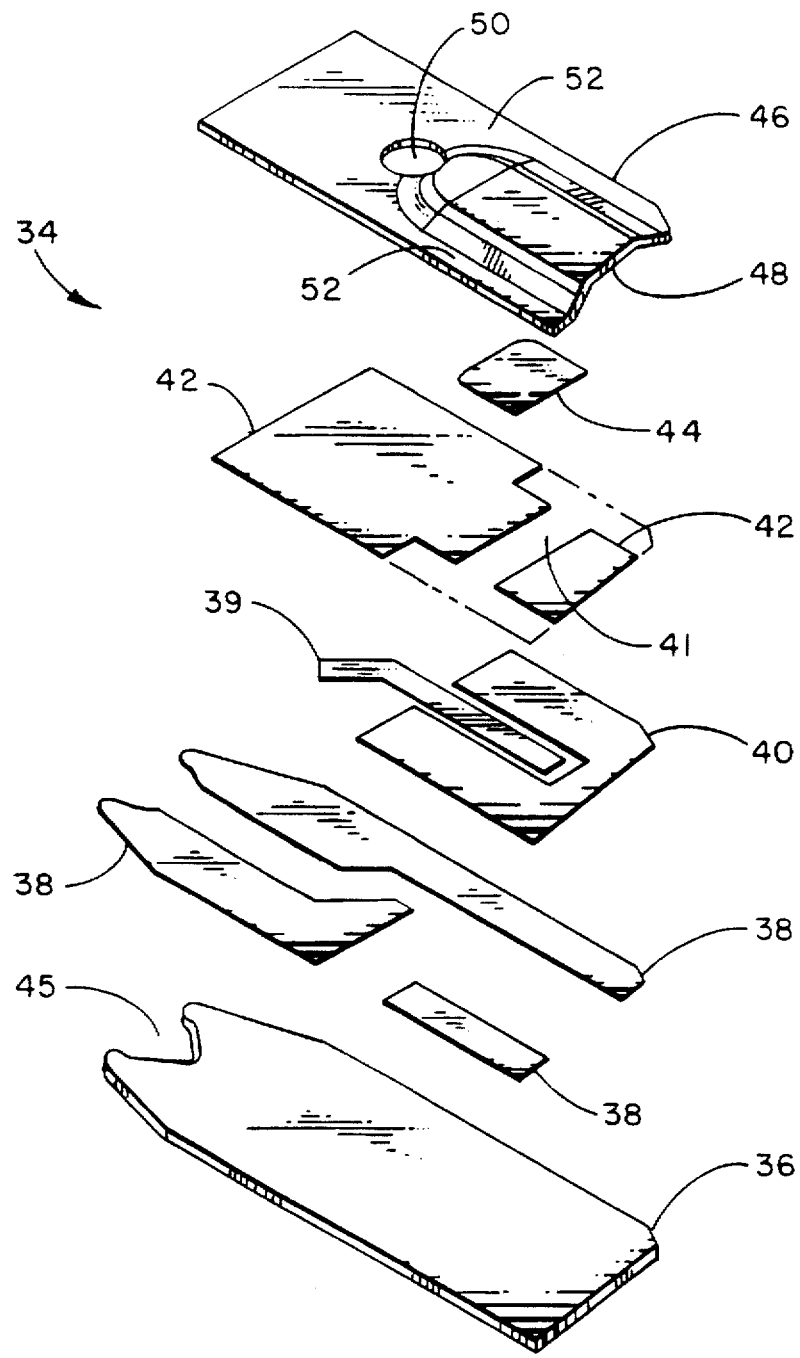
FIG. 1 is a sensor of the present invention.

The construction of the sensor with which the present invention is concerned is illustrated by FIG. 1. The sensor 34 is comprised of insulating base 36 upon which is printed in sequence (typically by screen printing techniques), an electrical conductor pattern 38, an electrode pattern (39 and 40), an insulating (dielectric) pattern 42 and finally a reagent layer 44. The function of the reagent layer is to convert glucose, or another analyte, stoichiometrically into a chemical species which is electrochemically measurable, in terms of current it produces, by the components in the electrode pattern. The reaction layer typically contains an enzyme which reacts with the analyte to produce mobile electrons on the electrode pattern and an electron acceptor such as a ferricyanide. The enzyme in the reaction layer can be combined with a hydrophilic polymer such as poly(ethylene oxide). The two parts 39 and 40 of the electrode print provide the working and reference electrodes necessary for the electrochemical determination. The electrode ink, which is about 14μ (0.00055") thick, typically contains electrochemically active carbon. Components of the conductor ink are a mixture of carbon and silver, chosen to provide a low chemical resistance path between the electrodes and the meter with which they are in operative connection via contact with the conductor pattern at the fish-tail end of the sensor 45. The typical thickness of the entire structure is 6μ (0.00025"). The function of the dielectric pattern is to insulate the electrodes from the test sample except in a defined area near the center of the electrode pattern 41 to enhance the reproducibility of the sensor reading. A defined area is important in this type of electrochemical determination because the measured current is dependent both on the concentration of the analyte and the area of the electrode which is exposed to the analyte containing test sample. A typical dielectric layer comprises a UV cured acrylate modified polyurethane about 10μ (0.0004") thick. The lid 46, which provides a concave space 48, typically formed by embossing a flat sheet of the deformable material, is punctured to provide air vent 50, and joined to the base 36 in a sealing operation. The lid and base can be sealed together by sonic welding in which the base and lid are first aligned and then pressed together between a vibratory heat sealing member or horn and a stationary jaw. The horn is shaped such that contact is made only with the flat, non-embossed regions of the lid. Ultrasonic energy from a crystal or other transducer is used to excite vibrations in the metal horn. This mechanical energy is dissipated as heat in the plastic joint allowing the bonding of thermoplastic materials. The procedure is more fully described in U.S. Pat. Nos. 3,505,136; 3,573,139; 3,562,041 and 4,313,774. They can also be joined by use of an adhesive material on the underside of the lid. In this embodiment, the base and lid are first aligned and then pressed together by means of a heated metal plate which is shaped such that contact is made only with the flat, non-embossed regions of the lid 52. The adhesive coating on the bottom surface of the lid is thereby melted and serves to fuse the lid 46 and the base 36 together upon cooling. This adhesive coating is preferably a water dispersible polyurethane. A typical temperature for the heated plate is 165° with the pressure being 2200 p.s.i. Holding the lid and base together under these conditions of heat and pressure for 1¼ seconds provides the desired unitary sensor with the capillary space for acceptance of the fluid test sample. The polyurethane layer bonds to the topmost exposed layer (dielectric 42 with dotted edges) of the base under the flat regions of the lid. Alternatively, the edges of the dielectric are slightly narrowed (represented by dielectric layer 42 with solid edges) which allows the polyurethane to bond with the material of the electrode print pattern 40. This is a preferred configuration because the bond strength between the adhesive and the electrode ink is greater than that between the adhesive and the dielectric material thereby providing a more leakproof capillary space.

Suitable materials for the insulating base include polycarbonate, polyethylene terephthalate and dimensionally stable vinyl and acrylic polymers as well as polymer blends such as polycarbonate/polyethylene terephthalate and metal foil structures such as a nylon/aluminum/polyvinyl chloride laminate. The lid is typically fabricated from a deformable polymeric sheet material such as polycarbonate or an embossable grade of polyethylene terephthalate, glycol modified polyethylene terephthalate or a metal foil composition such as an aluminum foil structure. The dielectric layer can be fabricated from an acrylate modified polyurethane which is curable by UV light or moisture or a vinyl polymer which is heat curable.

The present invention facilitates the use of an embossed lid (46, FIG. 1) as opposed to the use of a spacer as in the prior art sensor elements in which, instead of embossing, the two sides of the capillary space are formed from a spacer element. The use of the embossed lid enables one to avoid the use of an extra part, i.e. the spacer, and a number of processing steps. The steps involved in assembling the spacer containing sensor are:

i. preparing the complete electrode structures including the reagent layer; an agent to induce wicking of blood into the capillary space needs to be included in the uppermost layer;

ii. adding an additional layer containing an agent to induce wicking of blood into the capillary space; this layer may be avoided if the agent is included in the chemistry layer;

iii. die cutting a capillary channel into the spacer material which is typically a laminate of release/liner/adhesive/ spacer material/adhesive/release liner;

iv. stripping the release liner from one side of the spacer material and attaching the spacer to the base; and v. stripping the release liner and assembling the lid to the other side of the spacer.

The present invention permits one to manufacture a sensor by:

i. printing electrodes onto the base material and, optionally, applying the reagent layer onto the electrodes;

ii. optionally coating an adhesive layer onto the under surface of the lid;

iii. embossing the top and sides of the capillary space into the lid; and iv. mating the lid to the base and sealing them together by the application of heat.

The sensors of the present invention can be manufactured by mating an array of lids, i.e. a flat sheet of lidstock material having a plurality of concave indentations embossed therein, with a corresponding array of bases and then punching individual sensors from the array with a die after the lidstock and sheet of base material have been mated and heat sealed.

The construction of a sensor according to the present invention is accomplished according to the following general example:

GENERAL EXAMPLE

In this example, a large number of sensor lids are fabricated from a rolled sheet of polycarbonate which has been unrolled to provide a flat surface. This sheet is referred to as the lid stock since it will be the source of a multiplicity of lids.

A bifunctional coating solution, comprising an aqueous polyurethane dispersion, is spread on to one side of a polycarbonate sheet using a wire wound rod or a slot die coater and air dried. This material serves both as an adhesive to adhere the lid to the base and provides a wettable surface on the inside of the lid to enhance the ability of the capillary space to fill with test fluid. The dried coating thickness is 0.0007" to 0.002" (17μ to 50μ) with the wet coating thickness in the range of 0.0014" to 0.005" (35μ to 125μ) for a typical solids content of 40% to 50%. The bifunctional layer has some tack for a short period after drying and when the sheet is rewound a temporary liner or interleave is introduced in contact with the coating. After a period of a few hours, the initial tack is lost allowing the polycarbonate lid stock to be unrolled without damage to the coating. Suitable materials for the liner are polyolefins or polyethylene terephthalate.

The next stage of processing involves embossing of the concave areas and the punching of various holes in the polycarbonate sheet for registration and tracking before slit ribbons of lid stock are rolled up. It is essential that the adhesive be non-tacky so that it sticks to neither the embossing and punching tools nor to the polycarbonate support while rolled in ribbon form. It is also essential that the adhesive not form gummy deposits on the punching or embossing tools which would necessitate frequent cleaning.

The base stock, typically of polycarbonate, is printed with various inks to form the electrodes and then overcoated with a dielectric layer in a predetermined pattern designed to leave a desired surface of the electrode exposed. The bifunctional material must adhere to the dielectric material when the lid is mated directly to the dielectric layer. Alternatively part of the dielectric material can be deleted making it possible for the adhesive to contact the electrode material and, in some cases, form a better bond. In order to assemble the lidstock to the base, the continuous ribbon of lid stock is unwound and passed through a special laminator where it is registered and them combined with a strip of the base stock under the influence of heat and pressure. It is desirable for the heat sealing process to take about one second which requires an adhesive which is capable of very rapidly forming a strong bond. After heat sealing, the continuous ribbon of laminate is wound onto a reel.

In another embodiment, an aluminum foil structure (a three layer laminate consisting principally of nylon/aluminum/polyvinyl chloride) is used as the lid. Polyvinyl chloride is a thermoplastic and serves effectively as the heat-activated adhesive. This material is embossed and formed in the same way as described above and then gas plasma treated (0.6 torr of oxygen at 250W for 3.5 minutes). Before treatment the surface energy is 32 dynes/cm and after it is greater than 60 dynes/cm. After lamination to the vinyl base under conditions of heat and pressure, sensors are cut from the array.

In order to singulate individual sensors from the laminate ribbon, the laminate is passed through punching equipment in which individual sensors are punched from the array preparatory to being placed into a foil blister package for storage. In the preferred method of using the sensors, they are packaged in a circular disk having ten individual compartments arranged radially. The disk is made from an aluminum foil/plastic laminate which is sealed to isolate the sensor from ambient humidity and from other sensors with a burst foil cover, which disk is mounted within a specially designed instrument. To retrieve a sensor, a knife is driven down through the burst foil into an individual elongated compartment at the end closest to the hub of the disk and then moved radially toward the perimeter of the blister. In doing so, the knife engages the rear (fish tail) of the sensor in that compartment. Radial travel of the knife pushes the tip of the sensor out through the burst foil and through parts of the instrument such that the nose of the sensor is completely out of the instrument and ready to receive a fluid test sample, e.g. blood. For this stage, it is essential that the bond between the base and lid of the sensor withstand the sheer forces generated when the sensor bursts out through the foil. This method of providing a sensor ready for use is more fully described in U.S. Pat. No. 5,575,403.

In use, the sensor tip, containing the opening to the capillary space, is touched to a small drop of the fluid test sample which is typically blood produced by a finger prick. The blood is rapidly drawn up into the capillary space where the interaction with the enzyme is initiated and the instrument is signaled to initiate its timing sequence. It is essential that blood be drawn very rapidly into the capillary space, regardless of its spatial orientation in order that the timing sequence be initiated. The dimensions of the capillary space are typically on the order of 0.125 mm to 0.38 mm (0.005" to 0.015") in height and 2.5 mm to 3.75 mm (0.1" to 0.15") in width to facilitate the drawing of blood into the capillary space.

We claim:

1. An electrochemical sensor for the detection of an analyte in a fluid test sample which comprises from the bottom up:
   a) an insulating base plate;
   b) an electrode layer on said base plate;
   c) a lid of a deformable material which provides a concave area in the central portion thereof in such a manner that, when mated with the base plate, the lid and base plate form a capillary space in which the electrode layer is available for contact with the fluid test sample which is drawn into the capillary space by capillary action.

2. The sensor of claim 1 wherein the lid and base are held together by an adhesive layer.

3. The sensor of claim 2 wherein there is an adhesive layer on the side of the lid facing the base plate which layer substantially covers this side of the lid and is of a hydrophilic material to enhance the wettability of the capillary space formed by the mating of the lid and base plate.

4. The sensor of claim 2 wherein there is an adhesive layer on the side of the lid facing the base plate which layer substantially covers this side of the lid and is of a material which can be treated to enhance the wettability of the capillary space formed by the mating of the lid and base plate.

5. The sensor of claim 1 wherein there is a reaction layer comprising an enzyme which reacts with the analyte to produce mobile electrons on the electrode layer.

6. The sensor of claim 5 having a layer of dielectric material patterned over the electrode layer so that only a portion of the electrode layer, as predetermined by the pattern of the dielectric layer, is available for direct contact with the test fluid.

7. The sensor of claim 6 wherein the lid is configured so that its edges mate with the dielectric layer.

8. The sensor of claim 6 wherein the dielectric layer is configured so that it leaves a portion of the electrode layer exposed for direct contact with the edges of the lid.

9. The sensor of claim 5 wherein the enzyme in the reaction layer is combined with a hydrophilic polymer.

10. The sensor of claim 9 wherein the reaction layer also contains an electron acceptor.

11. The sensor of claim 10 wherein the electron acceptor is a ferricyanide.

12. The sensor of claim 9 wherein the hydrophilic polymer is poly(ethylene oxide).

13. The sensor of claim 1 wherein the concave area is formed by embossing a flat sheet of the deformable material.

14. A method for the preparation of an electrochemical sensor which comprises mating a base which carries an electrode structure on its surface with a lid of a deformable material which provides a concave space to form three sides of a capillary space which lid and base provide an electrochemical sensor having a capillary space which is open to the atmosphere with an electrode structure on the surface of the base and exposed to the capillary space.

15. The method of claim 14 wherein the lid has an adhesive on its underside which causes it to adhere to the base.

16. The method of claim 15 wherein the adhesive is heat activated and the lid is fastened to the base by heat sealing to thereby activate the adhesive and seal the lid to the base upon cooling.

17. The method of claim 15 wherein the adhesive on the underside of the lid is a hydrophilic material so that when the lid and base are mated to form the capillary space the wettability of the capillary space is enhanced.

18. The method of claim 14 wherein the lid and base are caused to adhere to each other by sonic welding.

19. The method of claim 14 wherein the electrode structure carries an oxidoreductase and an electron acceptor distributed in a hydratable polymer matrix on its surface.

20. The method of claim 19 wherein the oxidoreductase is glucose oxidase and the electron acceptor is a ferricyanide.

21. The method of claim 14 wherein the hydratable polymer matrix is comprised of poly(ethylene oxide).

22. A method for the production of a multiplicity of electrochemical sensors which comprises:

a) providing a sheet of a deformable material and a base sheet of an insulating material bearing a pattern of formed electrodes on its surface, wherein the sheet of deformable material has a substantially uniform layer of a thermally fusible material on a surface thereof;

b) embossing the sheet of deformable material to form a series of concave zones in the sheet which mirror the pattern of electrodes on the base sheet;

c) mating the sheet of deformable material to the base sheet so that the concave zones in the sheet of deformable material substantially encompass the electrodes and sealing these two sheets together by the application of sufficient heat and pressure to fuse the fusible adhesive; and d) punching individual sections from the fused sheets using a die of an appropriate shape to provide individual sensors comprising a capillary space circumscribed on three sides by the concave zone from the sheet of deformable material and on the bottom by the punched out portion of the base sheet to provide a sensor having a capillary space open to the atmosphere within which resides an electrode which is available for contact with a fluid test sample which is drawn into the capillary space by capillary action.

23. The method of claim 22 wherein there is a reaction layer comprising an enzyme which reacts with an analyte carried by the test fluid to provide mobile electrons when the test fluid is introduced into the capillary space.

24. The method of claim 23 wherein the enzyme and an electron acceptor are combined with a hydrophilic polymer to form a reaction layer on the surface of the electrode.

25. The method of claim 22 wherein the fusible adhesive comprises a material which is sufficiently hydrophilic to enhance the wettability of the capillary space.

* * * * *